United States Patent [19]

Beck

[11] Patent Number: 5,622,992

[45] Date of Patent: Apr. 22, 1997

[54] TOPICAL AROMATIC RELEASING COMPOSITIONS

[75] Inventor: William F. Beck, Batavia, Ohio

[73] Assignee: The Procter & Gamble Company, Cincinnati, Ohio

[21] Appl. No.: 612,197

[22] Filed: Mar. 7, 1996

Related U.S. Application Data

[63] Continuation of Ser. No. 316,704, Sep. 30, 1994, abandoned, which is a continuation of Ser. No. 171,872, Dec. 22, 1993, abandoned, which is a continuation of Ser. No. 56,010, Apr. 30, 1993, abandoned.

[51] Int. Cl.$^6$ .................................................. A61K 31/16
[52] U.S. Cl. .................. 514/613; 514/625; 514/849; 514/850; 514/853; 514/617
[58] Field of Search ..................................: 514/613, 617, 514/853, 854, 850, 625, 849

[56] References Cited

U.S. PATENT DOCUMENTS

| | | | |
|---|---|---|---|
| 2,798,053 | 7/1957 | Brown et al. | |
| 4,136,164 | 1/1979 | Rowsell et al. | 424/54 |
| 4,150,052 | 4/1979 | Watson et al. | 260/557 R |
| 4,153,679 | 5/1979 | Rowsell et al. | 424/45 |
| 4,230,688 | 10/1980 | Rowsell et al. | 424/45 |
| 4,248,859 | 2/1981 | Rowsell et al. | 424/54 |
| 4,318,900 | 3/1982 | Rowsell et lal. | 424/54 |
| 4,509,949 | 4/1985 | Huang et al. | 586/558 |
| 4,534,960 | 8/1985 | Chavkin | 424/49 |
| 4,883,660 | 11/1989 | Blackman et al. | 424/78 |
| 4,927,631 | 5/1990 | Bates | 424/195.1 |
| 4,971,798 | 11/1990 | Coia et al. | 424/440 |
| 4,980,169 | 12/1990 | Oppenheimer et al. | 424/439 |
| 5,073,366 | 12/1991 | Beck | 424/720 |
| 5,073,371 | 12/1991 | Turner et al. | 424/401 |
| 5,087,445 | 2/1992 | Haffey et al. | 424/59 |
| 5,322,689 | 6/1994 | Hughes et al. | 424/401 |

OTHER PUBLICATIONS

B.F. Goodrich Technical Data Sheet No. 73, Carbopol® 1342 (1984).
B.F. Goodrich Technical Bulletin SP–1, Product Data Specialty Polymers and Chemicals Division (Jul. 1982).
Clinical Otolaryngol, 1988 13, pp. 25–29; "The effects of menthol isomers on nasal sensation of airflow", R. Eccles, D.H. Griffiths, C.G. Newton & N.S. Tolley.
J. Pharm. Pharmacol, 1990, 42, pp. 652–654 "The effects of oral administration of (–)menthol on nasal resistance to airflow and nasal sensation of airflow in subjects suffering from nasal congestion associated with the common cold", R. Eccles, M.S. Jawas, S. Morris.

*Primary Examiner*—Theodore J. Criares
*Attorney, Agent, or Firm*—David K. Dabierre; Douglas C. Mohl; Jacobus C. Rasser

[57] ABSTRACT

The present invention relates to topical aromatic releasing compositions containing one or more volatile aromatic compounds selected from the group consisting of 3-1-menthoxy propane-1,2-diol, N-substituted-p-menthane-3-carboxamides and acyclic carboxamides and mixtures thereof. In further embodiments, these compositions are also useful for providing relief from nasal symptoms.

3 Claims, No Drawings

TOPICAL AROMATIC RELEASING COMPOSITIONS

This is a continuation of application Ser. No. 08/316,704, filed on Sep. 30, 1994, now abandoned, which is a continuation of application Ser. No. 08/171,872, filed on Dec. 22, 1993, now abandoned, which is a continuation of application Ser. No. 08/056,010, filed on Apr. 30, 1993, now abandoned.

TECHNICAL FIELD

The present invention relates to topical aromatic decongestant pharmaceutical compositions for nasal administration. In particular, it relates to such topical aromatic compositions containing one or more volatile aromatic compounds selected from the group consisting of 3-1-menthoxy propane-1,2-diol, N-substituted-p-menthane-3-carboxamides and acyclic carboxamides and mixtures thereof along with a pharmaceutically-acceptable aqueous carrier.

BACKGROUND OF THE INVENTION

The common cold, although not usually highly prevalent, discomforting and annoying infliction. The term "common cold" is applied to minor respiratory illnesses caused by a variety of different respiratory viruses. While rhinoviruses are the major known cause of common colds, accounting for approximately 30 percent of colds in adults, viruses in several other groups are also important. While immune responses occur, and infection with some respiratory tract viruses therefore could be prevented by a vaccine, development of a polytypic vaccine to cover all possible agents is impractical. Thus, the problem of controlling acute upper respiratory disease presents complex challenges, and the long-desired discovery of a single cure for the common cold is an unrealistictic expectation.

With rhinovirus infection, symptoms of nasal discharge, nasal congestion, and sneezing usually commence on the first day of illness and progress to maximum severity by the second or third day. The costs of treating colds with over-the-counter medications in the United States is estimated at an annual cost of over 1.5 billion dollars. The direct costs of treatment in outpatient clinics is estimated at almost four billion dollars. Indirect costs, based on the amount of loss in wages because of restricted activity are substantially higher.

At present, only symptomatic treatment is available for the common cold; the majority of these drugs are taken orally. Exemplary prior art oral compositions for treatment of nasal and other cold, flu, allergy and sinus symptoms and the discomfort, pain, fever and general malaise associated therewith generally contain an analgesic (aspirin or acetaminophen) and one or more antihistamines, decongestants, cough suppressants, antitussives and expectorants. Other specific pharmaceutical actives for nasal symptoms (e.g., congestion) generally contain either oxymetazoline or phenylephrine. These actives are generally delivered topically to the nasal mucosa via a nasal spray. For individuals with certain medical conditions such as heart disease, hypertension, diabetes or thyroid disorders, oral drugs such as decongestants could pose a risk of unfavorable drug interactions and may cause an adverse reaction. It would, therefore, be highly desirable to deliver relief from specific nasal symptoms via compositions without the need for such pharmaceutical actives.

Nasal delivery of therapeutic agents has been well known for a number of years. See, for example, U.S. Pat. No. 4,749,700 to Wenig, issued Jun. 7, 1988, U.S. Pat. No. 4,778,810 to Wenig, et al., issued Oct. 18, 1988 and U.S. Pat. No. 4,729,997 to Wenig issued Mar. 8, 1988. Nasal saline sprays have been used to moisturize nasal passages and to dissolve build-up in the nasal mucosa; however, saline solutions alone have not proved satisfactory for relief of nasal congestion. Menthol has been administered orally from lozenges and the like as well as delivered to the nasal mucosa from an inhaler containing a wick and no other excipients, see, for example, Clinical Otolaryngology, 1988, vol. 13, pps. 25–29. Yet menthol delivered in such a manner has not been found to provide a sufficient level of relief.

It has been discovered that topical aromatic decongestant pharmaceutical compositions containing one or more volatile aromatic compounds selected from the group consisting of 3-1-menthoxy propane-1,2-diol, N-substituted-p-menthane-3-carboxamide carboxamides and mixtures thereof provides the user with improved actual and/or perceived relief from nasal symptoms such as congestion and the like without the need for pharmaceutical actives such as oxymetazoline. In addition, such compositions will not cause drowsiness or other side effects attendant with oral decongestants.

It is therefore an object of the present invention to provide topical aromatic decongestant compositions which provide treatment for nasal symptoms resulting from, for example, colds, flu, allergy and sinus. It is a further object of the present invention to provide compositions which provide the user with improved actual and/or perceived relief from nasal symptoms such as congestion and the like without the need for pharmaceutical actives. It is still a further object of the present invention to provide compositions which minimize the likelihood of adverse drug interactions and further which provide for proper medication management.

SUMMARY OF THE INVENTION

The present invention relates to topical aromatic decongestant compositions for nasal administration consisting essentially of:

(a) from about 0.001% to about 1% of one or more volatile aromatic compounds selected from the group consisting of 3-1-menthoxy propane-1,2-diol, N-substituted-p-menthane3-carboxamides and acyclic carboxamides and mixtures thereof;

(b) from about 0.01% to about 99.99% of a pharmaceutically acceptable aqueous saline solution carrier.

The present invention also relates to a method for treatment of nasal symptoms comprising administering a safe and effective amount of these topical aromatic releasing decongestant compositions. By nasal symptoms is meant congestion, dryness, irritation, runny nose, blockage and the like.

All levels and ratios are by weight of the total composition, unless otherwise indicated.

DETAILED DESCRIPTION OF THE INVENTION

The compositions of the present invention contain the essential components as well as various optional components as indicated below.

More specifically, the compositions of the instant invention are for nasal administration and contain a therapeutically effective amount of the selected aromatic agent or agents. They are preferably provided as isotonic aqueous solutions, suspensions or viscous compositions which may be buffered to a selected pH.

Aromatic Component.

The first essential component of the present invention is an volatile aromatic component. This aromatic component comprises from about 0.001% to about 1%, preferably from about 0.1% to about 0.5% and most preferably from about 0.1% to about 0.3% of one or more volatile aromatic compounds selected from the group consisting of 3-1-menthoxy propane-1,2-diol, N-substituted-p-menthane-3-carboxamides and acyclic carboxamides and mixtures thereof. While not to be limited by theory, it is believed that the benefits obtained by the use of these coolants in the compositions of the present invention are the result of the unique cooling profiles for these compounds.

3-1-menthoxy propane 1,2-diol is fully described in detail in U.S. Pat. No. 4,459,425, issued Jul. 10, 1984 to Amano et. al, incorporated herein by reference in its entirety. This volatile aromatic is commercially available, being sold by Takasago Perfumery Co., Ltd., Tokyo, Japan.

The N-substituted-p-menthane-3-carboxamides are fully described in U.S. Pat. No. 4,136,163 to Watson et al., issued Jan. 23, 1979 incorporated herein by reference in its entirety. The most preferred volatile aromatic of this class is N-ethyl-p-menthane-3-carboxamide which is commercially available as WS-3 from Wilkinson Sword Limited.

Useful acyclic carboxamides are more full described in U.S. Pat. No. 4,230,688 to Rowsell et al., issued Oct. 28, 1980 incorporated herein by reference in its entirety. The most preferred volatile aromatic of this class is N,2,3-trimethyl-2-isopropylbutanamide which is commercially available as WS-23 from Wilkinson Sword Limited.

Preferred for use herein is a mixture of 3-1-menthoxy propane 1,2-diol and N-ethyl-p-menthane-3-carboxamide, preferably in a weight ratio of about 3:1, respectively. The most preferred composition contains a mixture of 3-1-menthoxy propane 1,2-diol, N-ethyl-p-menthane-3-carboxamide and N,2,3-trimethyl-2-isopropylbutanamide, preferably in a weight ratio of 2:1:1, respectfully.

Pharmaceutically-acceptable Aqueous Nasal Carrier.

The second essential component of the present invention is a pharmaceutically-acceptable aqueous carrier. Preferred for use herein are aqueous saline solution carriers. These solutions which generally contain sodium chloride as the salt are fully described in Remington's Pharmaceutical Sciences, 17th edition (1985) p. 835, which is hereby incorporated by reference herein. The salt is present in the solution at a level of about 0.01% to about 2%, preferably from about 0.5% to about 1.0% and most preferably from about 0.5% to about 0.75%.

Any of the aromatics identified above can be conveniently administered nasally to warm-blooded animals to elicit the desired therapeutic response by formulating it into a nasal dosage form, together with a nontoxic pharmaceutically-acceptable nasal carrier. As indicated earlier, the aromatic can be employed in compositions of the present invention. Suitable nontoxic pharmaceutically-acceptable nasal carriers are known to those skilled in the art and are also fully disclosed in Remington's Pharmaceutical Sciences, 17th edition, 1985, which is hereby incorporated by reference herein. Obviously, the choice of suitable carrier forms will depend on the exact nature of the particular nasal dosage form required, e.g., whether the drug is to be formulated into a nasal solution (for use as drops or as a spray), a nasal suspension, a nasal ointment, a nasal gel or another nasal form. Preferred nasal dosage forms are solutions, suspensions and gels, which normally contain sodium chloride in a major amount of water (preferable purified water) in addition to the aromatic. Minor amounts of other ingredients such as pH adjusters (e.g., a base such as NaOH), emulsifiers or dispersing agents, buffering agents, preservatives, wetting agents and jelling agents (e.g., methylcellulose) may also be present.

Most preferably, the nasal composition is isotonic, i.e., it has the same osmotic pressure as blood and lacrimal fluid. If desired, sustained release nasal compositions, e.g., sustained release gels can be conveniently employed.

Those skilled in the art will be aware that a therapeutically effective amount of a particular agent will vary with the particular agent, the age, size, weight and general physical condition of the patient; however, the advantage of the present invention over conventional topical nasal decongestants containing pharmaceutical actives is that the compositions of the present invention can be used as frequently as desired.

As a practical matter the selected therapeutic compositions will normally be prepared in dosage unit forms to contain therapeutically effective amounts of the selected aromatic. In specific instances fractions of the dosage units or multiple dosage units will be employed. Typically dosage units may be prepared to deliver from about 0.01 mg to about 5 mg, preferably from about 0.5 mg to about 1 mg and most preferably from about 0.1 mg to about 0.5 mg of aromatic agent per dose (e.g., 50 mg to about 150 mg of spray). A typical dose contains two to three sprays per nostril.

The desired isotonicity of the compositions of this invention may be accomplished using, for example, the sodium chloride already present, or other pharmaceutically-acceptable agents such as dextrose, boric acid, sodium tartrate, sodium phosphate, potassium phosphate, propylene glycol or other inorganic or organic solutes. Sodium chloride is preferred particularly for buffers containing sodium ions.

Viscosity of the compositions may be maintained at the selected level using a pharmaceutically-acceptable thickening agent. Methyl cellulose is preferred because it is readily and economically available and is easy to work with. Other suitable thickening agents include, for example, xanthan gum, carboxymethyl cellulose, hydrozypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

Preferred compositions within the scope of this invention will contain from about 0.01% to about 5% of a humectant to inhibit drying of the mucous membrane and to prevent irritation. Any of a variety of pharmaceutically-acceptable humectants can be employed including, for example sorbitol, propylene glycol or glycerol. As with the thickeners, the concentration will vary with the selected agent, although the presence or absence of these agents, or their concentration is not an essential feature of the invention.

Enhanced absorption across the nasal membrane can be accomplished employing a therapeutically acceptable surfactant. Typical useful surfactants for these therapeutic compositions include polyoxyethylene derivatives of fatty acid partial esters of sorbitol anhydrides such as Tween 80, Polyoxyl 40 Stearate, Polyoxylethylene 50 Stearate and Octoxynol, as well as Oxyethylated tertiary octyl phenol formaldehyde polymer (available from Sterling Organics as tyloxapol). The usual concentration is from 0.5% to 10% based on the total weight.

A pharmaceutically-acceptable preservative is generally employed to increase the shelf life of the compositions. Benzyl alcohol is suitable, although a variety of preservatives including, for example, parabens, thimerosal, chlorobutanol, phenylmecuric acetate or benzalkonium chloride may also be employed. The most preferred preservative system for use herein comprises a combination of benzalkonium chloride, chlorhexidine gluconate and disodium EDTA. A suitable concentration of the preservative will be from 0.001% to 2% based on the total weight, although there may be appreciable variation depending upon the agent selected.

Aromatics.

Various other aromatic components (e.g., aldehydes and esters) may also be used. These aromatics include, for example, menthol, camphor, eucalyptol, benzaldehyde (cherry, almond); citral (lemon, lime); neral; decanal (orange, lemon); aldehyde C-8, aldehyde C-9 and aldehyde C-12 (citrus fruits); tolyl aldehyde (cherry, almond); 2,6-dimethyl-octanal (green fruit); and 2-dodecenal (citrus, mandarin). Mixtures of these aromatics can also be used.

Other Optional Components.

A variety of additional ingredients may be added to the emulsion compositions of the present invention. These additional ingredients include various polymers for aiding the film-forming properties and substantivity of the formulation, preservatives for maintaining the antimicrobial integrity of the compositions, antioxidants, and agents suitable for aesthetic purposes such as fragrances, pigments, and colorings.

The compositions can also contain low levels of insoluble ingredients added, for example for visual effect purposes, e.g. thermochromic liquid crystalline materials such as the microencapsulated cholesteryl esters and chiral nematic (nonsterol) based chemicals such as the (2-methylbutyl) phenyl 4-alkyl(oxy)benzoates available from Hallcrest, Glenview, Ill. 60025, U.S.A.

The pH of the compositions is preferably from about 5 to about 9, more preferably from about 5.5 to about 7.

Preferably the composition is applied to the nasal mucosa via topical application of a safe and effective amount of the composition to treat nasal symptoms. The amount of aromatic agent and frequency of topical application to the nasal mucosa can vary widely, depending upon personal needs, but it is suggested as an example that topical application range from about once per day to about twenty times daily, preferably from about twice per day to about ten times daily with use of from about 0.01 mg to about 5 mg of aromatic agent per dose (e.g., 50 mg to about 150 mg of spray).

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE I

A topical nasal aromatic composition is prepared by combining the following components utilizing conventional mixing techniques.

| Ingredients | W/W % |
| --- | --- |
| Tyloxapol | 0.700 |
| Sodium Phosphate | 0.100 |
| Potassium Phosphate | 0.350 |
| Sodium Chloride | 0.650 |
| 3-l-menthoxy propane 1,2-diol | 0.007 |
| N-ethyl-p-menthane-3-carboxamide | 0.003 |
| Disodium EDTA | 0.010 |
| Benzalkonium Chloride (50%) | 0.040 |
| Chlorhexidine Gluconate (20%) | 0.270 |
| Water, Purified QS. | 100.000 |

Tyloxapol and water are added to an appropriately sized vessel and completely mixed under low heat. Ingredients are added one at a time with mixing, allowing each to dissolve before adding the next. The aromatic are blended together in a separate premix before being added to the batch. A separate premix is also made for chlorhexidine gluconate. After all ingredients have been added, purified water is used to bring the batch to the appropriate weight.

Administration of approximately 0.5 grams of the composition is used for topical nasal application to provide relief from nasal symptoms.

EXAMPLE II

A topical nasal aromatic composition is prepared by combining the following components utilizing conventional mixing techniques.

| Ingredients | W/W % |
| --- | --- |
| Pluronic L-44 | 2.500 |
| Sodium Phosphate | 0.100 |
| Potassium Phosphate | 0.350 |
| Sodium Chloride | 0.650 |
| 3-l-menthoxy propane 1,2-diol | 0.007 |
| N-ethyl-p-menthane-3-carboxamide | 0.003 |
| N,2,3-trimethyl-2-isopropylbutanamide | 0.003 |
| Disodium EDTA | 0.010 |
| Benzalkonium Chloride (50%) | 0.040 |
| Chlorhexidine Gluconate (20%) | 0.270 |
| Water, Purified QS. | 100.000 |

Administration of approximately 0.5 grams of the composition is used for topical nasal application to provide relief from nasal symptoms.

EXAMPLE III

A topical nasal aromatic composition is prepared by combining the following components utilizing conventional mixing techniques.

| Ingredients | W/W % |
| --- | --- |
| Tyloxapol | 0.700 |
| Sodium Phosphate | 0.100 |
| Potassium Phosphate | 0.350 |
| Sodium Chloride | 0.650 |
| 3-l-menthoxy propane 1,2-diol | 0.007 |
| N-ethyl-p-menthane-3-carboxamide | 0.003 |
| N,2,3-trimethyl-2-isopropylbutanamide | 0.003 |
| Parabens | 0.300 |
| Water, Purified QS. | 100.000 |

Administration of approximately 0.5 grams of the composition is used for topical nasal application to provide relief from nasal symptoms.

EXAMPLE IV

A topical nasal aromatic composition is prepared by combining the following components utilizing conventional mixing techniques.

| Ingredients | W/W % |
| --- | --- |
| Tyloxapol | 0.700 |
| Sodium Phosphate | 0.100 |
| Potassium Phosphate | 0.350 |
| Sodium Chloride | 0.650 |
| 3-l-menthoxy propane 1,2-diol | 0.007 |
| N-ethyl-p-menthane-3-carboxamide | 0.003 |
| N,2,3-trimethyl-2-isopropylbutanamide | 0.003 |
| Menthol | 0.034 |
| Benzalkonium Chloride | 0.200 |
| Water, Purified QS. | 100.000 |

Administration of approximately 0.5 grams of the composition is used for topical nasal application provide relief from nasal symptoms.

What is claimed is:

1. A method for treatment of nasal symptoms comprising administrating a safe and effective amount of topical aromatic releasing decongestant composition, wherein said composition consists essentially of:
   (a) from about 0.001% to about 1% of a mixture of at least two volatile aromatic compounds selected from the group consisting of 3-1-menthoxypropane-1,2-diol, N-substituted-p-menthane-3-caroxamides, and acylic carboxamides; and
   (b) from about 0.01% to about 99.9% of a pharmaceutically-acceptable aqueous solution carrier;
wherein said composition is free of pharmaceutically-active decongestants.

2. A method according to claim 1 wherein said mixture of aromatic compounds comprises 3-1-menthoxypropane-1,2-diol, N-substituted-p-menthane-3-carboxamides, and acyclic carboxamides, in a ratio 2:1:1, respectively, and wherein the pharmaceutically-acceptable aqueous solution carrier comprises from about 0.01% to about 2% of salt.

3. A method according to claim 1 wherein said mixture of aromatic compounds comprises 3-1-menthoxypropane-1,2-diol, and N-substituted-p-menthane-3-carboxamide, in a ratio of about 3:1.

* * * * *